US008834923B2

(12) United States Patent
Berthoumieu et al.

(10) Patent No.: US 8,834,923 B2
(45) Date of Patent: Sep. 16, 2014

(54) SLOW-RELEASE COMPOSITION, METHOD FOR THE PREPARATION THEREOF, AND USE THEREOF

(75) Inventors: Didier Berthoumieu, Villenouvelle (FR); Pierre Dupinay, Toutens (FR); Philippe Trannoy, Toulouse (FR)

(73) Assignee: Pierre Fabre Medicament, Boulogne Billancourt (FR)

( * ) Notice: Subject to any disclaimer, the term of this patent is extended or adjusted under 35 U.S.C. 154(b) by 1053 days.

(21) Appl. No.: 12/085,501

(22) PCT Filed: Nov. 23, 2006

(86) PCT No.: PCT/FR2006/002577
§ 371 (c)(1),
(2), (4) Date: May 22, 2008

(87) PCT Pub. No.: WO2007/063200
PCT Pub. Date: Jun. 7, 2007

(65) Prior Publication Data
US 2009/0162429 A1 Jun. 25, 2009

(30) Foreign Application Priority Data
Dec. 1, 2005 (FR) .................................... 05 12189

(51) Int. Cl.
*A61K 9/48* (2006.01)
*A61K 9/16* (2006.01)
*A61K 33/26* (2006.01)
*A61K 31/285* (2006.01)
*A61K 9/50* (2006.01)
*A61K 9/00* (2006.01)
*A61K 9/20* (2006.01)

(52) U.S. Cl.
CPC ............... *A61K 33/26* (2013.01); *A61K 9/0056* (2013.01); *A61K 31/285* (2013.01); *A61K 9/5026* (2013.01); *A61K 9/2081* (2013.01)
USPC ......................................................... 424/452

(58) Field of Classification Search
CPC ... A61K 9/5026; A61K 33/26; A61K 9/4858; A61K 33/24; A61K 9/2081; A61K 9/50; A61P 7/06
USPC .................................. 424/452, 497, 646, 490
See application file for complete search history.

(56) References Cited

U.S. PATENT DOCUMENTS 5,286,493 A 2/1994 Oshlack et al.
5,370,879 A * 12/1994 Masterson et al. ............ 424/490

(Continued)

FOREIGN PATENT DOCUMENTS

FR 2792527 10/2000
WO WO 95/14460 6/1995

(Continued)

OTHER PUBLICATIONS

Degussa; "Eudragit" [online] Jan. 2005 xpoo2399809.

(Continued)

*Primary Examiner* — Aradhana Sasan
(74) *Attorney, Agent, or Firm* — Hueschen and Sage

(57) ABSTRACT

The pharmaceutical or nutraceutical composition with sustained release of an active ingredient according to the present invention comprises at least one coated granule; the coated granule being composed of a particle that comprises said active ingredient and is coated with at least two coatings that comprise a combination of excipients. The present invention relates also to a process for the preparation of the composition.

30 Claims, 2 Drawing Sheets

(56) References Cited

U.S. PATENT DOCUMENTS

| | | | |
|---|---|---|---|
| 6,562,378 B1* | 5/2003 | Chandra | 424/601 |
| 6,613,361 B1* | 9/2003 | Lebon et al. | 424/497 |
| 2002/0034544 A1 | 3/2002 | Skinhoj et al. | |
| 2003/0035837 A1 | 2/2003 | Sackler et al. | |
| 2003/0180359 A1* | 9/2003 | Vergnault et al. | 424/468 |
| 2003/0190355 A1* | 10/2003 | Hermelin et al. | 424/468 |

FOREIGN PATENT DOCUMENTS

| | | |
|---|---|---|
| WO | 01/15665 | 3/2001 |
| WO | WO 01/45668 | 6/2001 |

OTHER PUBLICATIONS

French Preliminary Search Report for FR0512189 of Sep. 21, 2006.

International Search Report for PCT/FR2006/002577 of Apr. 25, 2007.

Written Opinion of The International Searching Authority for PCT/FR2006/002577 of Jul. 8, 2008.

Pivinik, A.V. Chronic Iron Deficiency Anemia, V mire lekarstv (In the world of medicaments) No. 3, 1999.

Chueshov, et al. Industrial Technology of Medicaments, vol. 2, pp. 360-362, The NFAU Publishing House, MYK Kniga, 2002.

Eudragit® RL 30 D, Product literature, Pharmacopeial Monographs, EVONIK Industries, accessed online 2010.

Eudragit® RS 30 D, Product literature, Pharmacopeial Monographs, EVONIK Industries, accessed online 2010.

Eudragit® RL 30 D and Eudragit® RS 30 D, Specifications and test methods, degussa, pp. 1-4, 2004.

Tardyferon®, Product literature, Pierre Fabre Pharma GmbH, 2004, and English language translation thereof.

\* cited by examiner

SLOW-RELEASE COMPOSITION, METHOD FOR THE PREPARATION THEREOF, AND USE THEREOF

The present invention relates to a pharmaceutical or nutraceutical composition for the sustained release of an active ingredient, to a process for the preparation thereof and to the use thereof in therapeutics. The active ingredient is preferably selected from the group of the minerals and oligoelements, and more especially the active ingredient is iron(II) sulfate.

Of all the nutriments, iron is one of those whose needs, in humans, are most difficult to cover in practice. Iron deficiency is a very widespread nutritional disorder throughout the world, and it affects primarily the developing countries but also, although to a lesser degree, the industrialised countries. Whatever the level of development, certain population groups are particularly at risk of developing an iron deficiency: these are mainly women of child-bearing age, and especially pregnant women, young children and adolescents.

Iron is present in the organism in a very small amount (50 mg/kg in men, 35 mg/kg in women). Some of this iron is used each day to meet the needs of the organism, those needs varying during life. In order to maintain adequate iron levels, losses must be made up from the dietary intake. Otherwise, an imbalance occurs and, depending on the moderate degree or advanced stage of the iron deficiency, this results in energy loss, diminished physical and intellectual performance, increased sensitivity to infections, disturbances during gestation, etc. This balance can be upset in the direction of deficiency in various circumstances: insufficient dietary intake or reduced absorption, increased losses, increased needs. One of the clinical consequences of iron deficiency is iron-deficiency anaemia, the harmful effects of which are well known. It is therefore necessary to ensure a sufficient iron intake, adapted to each individual, from food but also from food supplements and medicaments.

However, not much iron is absorbed by the organism (low intestinal absorption of from 10 to 20%). Its release profile must therefore be prolonged in order to overcome that low absorption.

The methods that are used today and are known to the person skilled in the art are principally methods of encapsulating the active ingredient by means of a polymer, a gelatin, starch, etc., methods of dissolving the active ingredient in a polymer matrix, or a combination of those two methods. Bioadhesive forms are also found, which allow the form to be kept at the site of its absorption. Increasing the contact time allows the local concentrations, and therefore the quantities that penetrate, to be increased. The nature of the polymers can be very varied (cellulose derivatives, methacrylic resins, etc.) and depends on the desired release profile. U.S. Pat. No. 6,402,997 relates to a method of preparing microcapsules based on soluble iron using a fatty acid ester (polyglycerine monostearate), the microcapsules being used in the field of food supplements.

Patent application WO 03/055475 relates to a controlled-release pharmaceutical formulation comprising venlafaxine: the formulation is in the form of a core comprising venlafaxine and various cellulose polymers; said core being coated with a polymeric agent composed of at least two polymers. The composition comprises a plurality of (at least four) different polymers, in specific and different ratios in the core and in the coating; this makes the preparation process long and complex.

At present, the proprietary medicine TARDYFERON® marketed by Pierre Fabre Médicament is indicated for the treatment of iron deficiencies. That product, which is based on iron(II) sulfate, has the advantages of being very well tolerated, of being stable over time (no phenomenon of oxidation of the ferrous iron) and of being released in a sustained manner in the organism. However, one of the excipients used is mucoproteose of animal origin. And it is precisely that mucoproteose that contributes to the resulting release profile and to protecting the ferrous iron against oxidation. However, the use of animal material gives rise to insurmountable disadvantages such as problems of microbiological safety, viral safety and possible difficulties with supply.

Consequently, it appears necessary to have available a novel formulation with sustained release of the active ingredient in order to overcome the problems associated with the use of an animal material in a pharmaceutical or nutraceutical composition, and more particularly when the active ingredient is an iron source.

To that end, the present invention relates to a pharmaceutical or nutraceutical composition based on an active ingredient associated with a combination of excipients as a replacement for mucoproteose, allowing said active ingredient to be released in a sustained manner.

The present invention relates also to a process for the preparation thereof and to the use thereof in the preparation of a pharmaceutical or nutraceutical product with sustained release of the active ingredient.

The pharmaceutical or nutraceutical composition with sustained release of an active ingredient according to the present invention comprises at least one coated granule; said coated granule being composed of a particle that comprises said active ingredient and is coated with at least two coatings, characterised in that they comprise a combination of excipients composed:

of at least one copolymer (a) of esters of acrylic acid and of methacrylic acid having a molar percentage of quaternary ammonium groups of less than or equal to 8%, in association with a second copolymer (b) of esters of acrylic acid and of methacrylic acid having a molar percentage of quaternary ammonium groups of greater than 8%, in a ratio by weight (a)/(b) of from 60/40 to 80/20, and with an amount of (a) of from 2.5% to 5.0% by dry weight, based on the total weight of the composition.

The quaternary ammonium groups contained in the copolymers (a) and (b) are present in different amounts; this gives the coatings obtained using those polymers different permeability properties. Copolymer (a) on its own forms coatings having low permeability, while copolymer (b) on its own forms coatings having high permeability.

It has now been found, interestingly, that the choice of excipients and especially of the two polymers (a) and (b) in a specific ratio allows a composition to be obtained that has a sustained release profile of the active ingredient for use in a therapeutic treatment for pharmaceutical or nutraceutical purposes, and more especially for use in the treatment and/or prevention of deficiencies of active ingredient when the active ingredient is an iron source. Furthermore, it has been noted, unexpectedly and surprisingly, that said composition also exhibits good stability and provides protection for the active ingredient in respect of oxidation.

Advantageously, the ratio by weight (a)/(b) of the two polymers according to the present invention is of the order of 70/30 and more advantageously of the order of 65/35. Advantageously, the amount by weight of copolymer (a) is from approximately 3.5% to approximately 4.0% by dry weight, based on the total weight of the composition, and is preferably approximately 3.9% by dry weight, based on the total weight of the composition.

The molar percentage of quaternary ammonium groups in copolymer (a) according to the present invention is preferably from approximately 2% to approximately 8%, more preferably from approximately 4% to approximately 6%, and yet more preferably approximately 5%. Advantageously, copolymer (a) is selected from the group comprising the copolymers of esters of acrylic acid and of methacrylic acid, and more advantageously it will be, for example, Eudragit RS30D® [Poly(ethyl acrylate-co-methyl methacrylate-co-trimethylammonioethyl methacrylate chloride) 1:2:0.1].

The molar percentage of quaternary ammonium groups in copolymer (b) according to the present invention is preferably from approximately 8% to approximately 12%, more preferably from approximately 9% to approximately 11%, and yet more preferably approximately 10%. Advantageously, copolymer (b) is selected from the group comprising the copolymers of esters of acrylic acid and of methacrylic acid, and more advantageously it will be, for example, Eudragit RL30D® [Poly(ethyl acrylate-co-methyl methacrylate-co-trimethylammonioethyl methacrylate chloride) 1:2:0.2].

Figure 1:
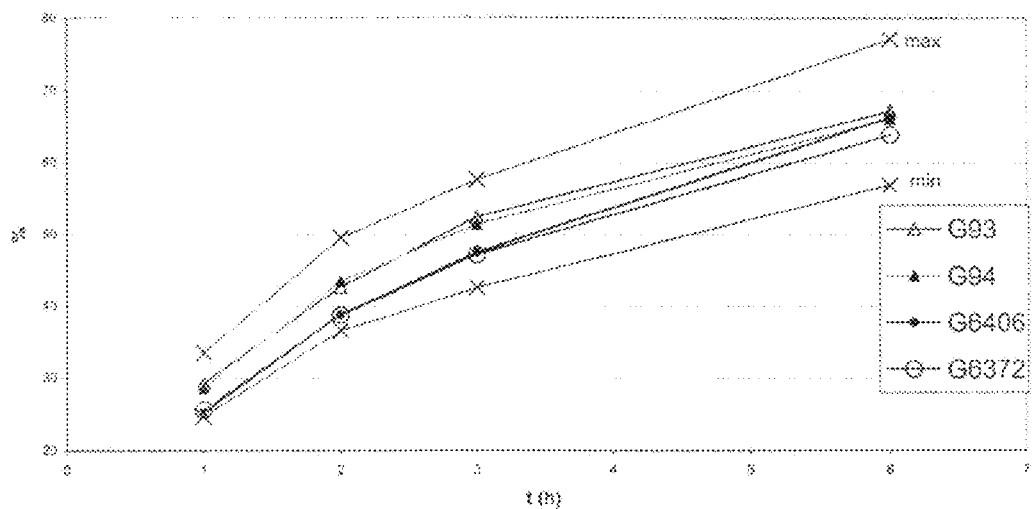
FIG. 1. The percentage dissolution of iron(II) sulfate as a function of time.

The invention will be better understood, and the aims, advantages and features thereof will become more clearly apparent, from the following description, which makes reference to the accompanying drawings showing non-limiting examples of the invention, in which:

FIG. 1 shows the percentage dissolution of iron(II) sulfate as a function of time (the measuring points have been chosen at 1, 2, 3 and 6 hours); for the two batches G93 (△) and G94 (▲) prepared according to Example 1 of the present invention and the two batches G6406 (•) and G 6372 (○) of TARDYFERON® with mucoproteose. Also shown are the minimum and maximum specifications (x) relating to the reference proprietary medicine TARDYFERON®. It will be noted that the dissolution profiles of the iron(II) sulfate in compositions according to the present invention are very similar to those obtained with two batches of TARDYFERON®. It is concluded that the composition according to the present invention allows the desired release profile to be obtained. Surprisingly, the composition as described by the present invention also allows the parameters of protection of the active ingredient against the phenomenon of oxidation to be retained. The wholly surprising aspect of the invention is that no antioxidant is necessary to ensure the stability of the active ingredient.

Figure 2:
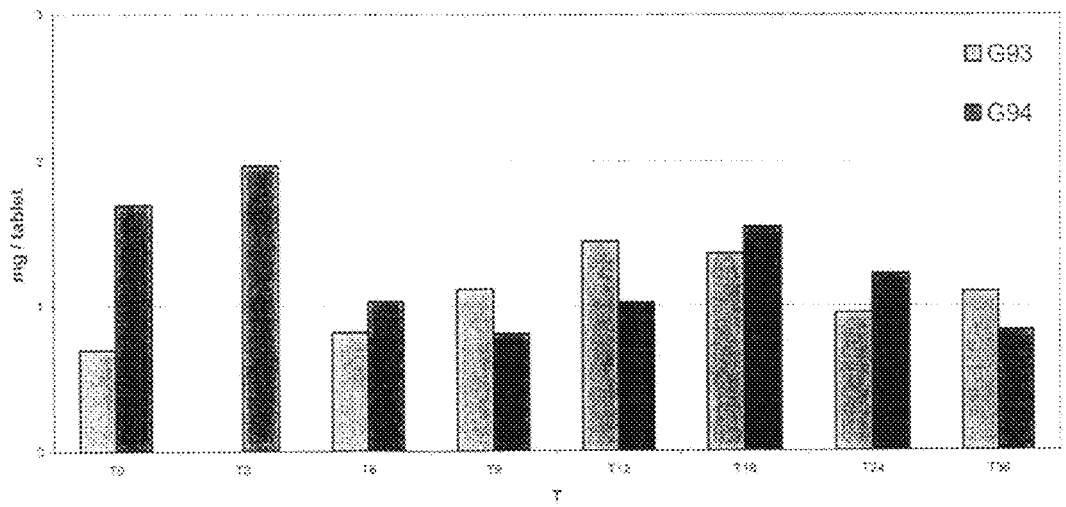
FIG. 2. Analysis of ferric iron (produced following oxidation of the ferrous iron) over time: measurements of ferric iron, in mg per tablet, were carried out at 0, 3, 6, 9, 12, 18, 24 and 36 months starting from tablets obtained from the same batches G93 (■) and G94 (■).
Figure 3:
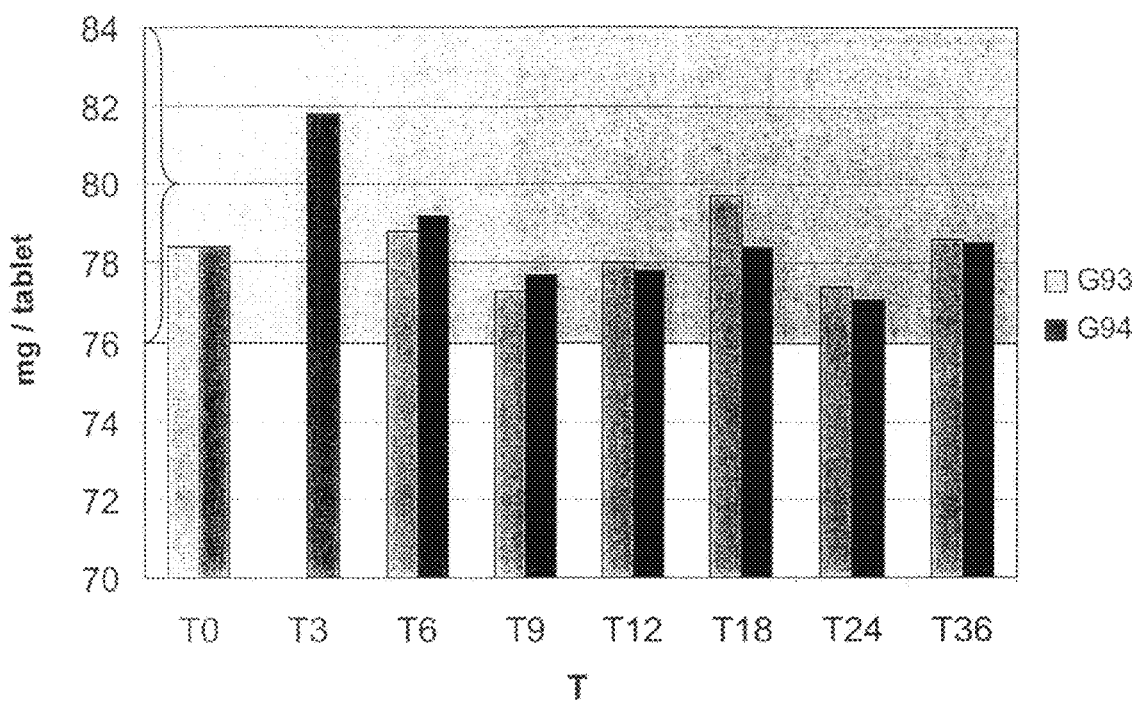
FIG. 3. Stability over time of the two batches G93 (■) and G94 (■).

FIGS. 2 and 3 show diagrammatically the stability results obtained over 36 months for the two batches prepared according to Example 1 of the present invention: FIGS. 2 and 3 relate, respectively, to the analysis of ferric iron and the analysis of total iron.

FIG. 2 shows the analysis of ferric iron (produced following oxidation of the ferrous iron) over time: measurements of ferric iron, in mg per tablet, were carried out at 0, 3, 6, 9, 12, 18, 24 and 36 months starting from tablets obtained from the same batches G93 (■) and G94 (■) as above. It will be noted that the results obtained are all below the maximum limit of 3.0 mg/tablet imposed in the specification relating to the reference proprietary medicine TARDYFERON® and that there is therefore no significant conversion of ferrous iron into ferric iron in the compositions according to the present invention. This result demonstrates the unexpected protective effect against oxidation of the composition that is used.

Finally, FIG. 3 demonstrates the good stability over time of those same two batches G93 (■) and G94 (■). The total iron, expressed in mg per tablet, contained in those tablets was analysed at different times T (at 0, 3, 6, 9, 12, 18, 24 and 36 months). The specifications relating to the reference proprietary medicine TARDYFERON® indicate that the amount of iron must be from 76 to 84 mg per tablet. It will be noted that all the analyses carried out are well within that range of values. It is concluded that there is no significant loss of total iron from the compositions according to the present invention.

Moreover, compared with the use of mucoproteose of animal origin, the advantages of an excipient formulation according to the invention are especially:
- improved safety of the product, especially viral safety;
- improved industrial feasibility in relation to the facilitated availability of the raw materials;
- a safe industrial process, because extraction from raw materials of animal origin in order to obtain mucoproteose is no longer necessary.

Another advantage of the composition according to the present invention is that said composition requires fewer excipients, qualitatively and quantitatively, than the proprietary medicine TARDYFERON®, which is reflected in this case in a lower cost price.

The preceding figures show the results obtained starting from a composition according to the present invention based on iron(II) sulfate as the sole source of active ingredient. However, it is possible reasonably to envisage that the benefits of the present invention can be extended to any composition comprising a pharmaceutical, nutraceutical, cosmetic or veterinary active ingredient with which it is desired to associate a sustained release profile. Mention may be made of antidepressants, antipyretics, vitamins and anti-inflammatories, for example. The active ingredient is preferably selected from the group comprising minerals and oligoelements, used on their own or in the form of a mixture.

Advantageously, the mineral is a source of iron(II) or iron (III) in the form of a salt or a complex. More advantageously, the iron salt is selected from the group comprising the sulfate, fumarate, gluconate, ascorbate, oxalate, succinate, glycerophosphate and feredetate.

Yet more advantageously, the active ingredient is iron(II) sulfate.

More advantageously, the iron complex is selected from the group composed of iron-dextran, iron-polymaltose and iron-protein complexes.

Advantageously, the composition comprises one or more pharmaceutically or nutraceutically acceptable substances selected from diluents, binders, lubricants, anti-agglomeration agents, plasticisers, used on their own or in the form of a mixture.

The plasticiser is advantageously selected in this case from the group formed by acetyl tributyl citrate, acetyl triethyl citrate, acetylated fatty acid glycerides, castor oil, diethyl sebacate, dibutyl sebacate, glycerol, glycerol monostearate, glyceryl triacetate, polyethylene glycols, polyoxyethylene/polyoxypropylene copolymers, propylene glycol, tributyl citrate, triethyl citrate, used on their own or in the form of a mixture, and is preferably triethyl citrate.

Advantageously, the diluent is selected from the group formed by celluloses and lactose and is preferably a cellulose.

Advantageously, the binder is selected from maltodextrins and povidones and is preferably a maltodextrin.

The present invention relates also to the use of the composition according to the present invention in a pharmaceutical or nutraceutical formulation with sustained release of the active ingredient. More particularly, the present invention relates to the use of such a formulation in the treatment and/or prevention of deficiencies of active ingredient, and more particularly deficiencies of minerals and oligoelements.

The term "pharmaceutical" within the scope of the present invention comprises formulations for the preparation of medicaments intended for preventive or curative treatment in human medicine and also in animal medicine.

More particularly, in the case where the active ingredient is an iron source, the composition according to the present invention is used in the preparation of a medicament intended for the treatment and/or prevention of iron deficiencies with or without anaemia.

More particularly, iron deficiency is iron-deficiency anaemia. Yet more particularly, the iron-deficiency anaemia is found in pregnant women; and such a use is employed when a sufficient dietary intake of iron cannot be ensured.

Advantageously, the composition according to the present invention is characterised in that it is in oral form.

The oral form is preferably selected from tablets, gelatin capsules, capsules, pastilles for sucking, and powders for drinkable suspensions and syrups.

Finally, the present invention relates to a process for the preparation of coated granules for a pharmaceutical or nutraceutical formulation according to the present invention, characterised in that it comprises the following steps:

1) the active ingredient is coated, in a blade mixer, with an aqueous dispersion of the two copolymers (a) and (b), the ratio by weight (a)/(b) of which is from 60/40 to 80/20, with an amount of (a) of from 2.5% to 5.0% by dry weight, based on the total weight of the composition,
2) the granules obtained in 1) are broken up,
3) the granules obtained in 2) are dried to a residual humidity of less than or equal to 3.5%,
4) the dried granules obtained in 3) are coated in a fluidised-air bed by atomisation of an aqueous dispersion of the two copolymers (a) and (b), the ratio by weight (a)/(b) of which is from 60/40 to 80/20, with an amount of (a) of from 2.5% to 5.0% by dry weight, based on the total weight of the composition,
5) the coated granules obtained in 4) are dried to a residual humidity of less than or equal to 3.5%,
6) the dry granules are sized and classified.

A fundamental feature of the process of the present invention is that it uses only water as solvent. This facilitates the implementation of said process and protects the operators, during manufacture, from the potential dangers associated with the use of organic solvents.

The process of the present invention accordingly involves two main steps 1) and 4). The release profile of said active ingredient is governed by this double coating of the particles of active ingredient.

Within the scope of the present invention, "coating" is understood as meaning the deposition of a layer of film-forming agent on a particle comprising especially the active substance.

Steps 1) to 3) allow a first granule to be obtained, characterised in that the residual humidity of the mixture at the end of step 3) is less than or equal to approximately 3.5% and is preferably from approximately 2.5% to approximately 3.5%.

Advantageously, the mixer used during step 1) is a mixer of the FIELDER® type or an equivalent mixer known to the person skilled in the art. In a particular embodiment of the invention, step 2), the breaking step, is carried out in an oscillating granulator equipped with a screen whose mesh size is defined as a function of the desired specification. The subsequent drying step can be carried out in various ways known to the person skilled in the art: more particularly, drying is carried out in a fluidised-air bed.

Steps 4) and 5) allow a second granule to be obtained, characterised in that the residual humidity of the mixture at the end of step 5) is less than or equal to approximately 3.5% and is preferably from approximately 2.5% to approximately 3.5%.

Advantageously, the sizing 6) is carried out in an oscillating granulator equipped with a screen whose mesh size is defined as a function of the desired specification.

It is possible for the granules so obtained at the end of step 6) to be packaged directly in the form of a powder for a drinkable suspension or for a syrup, for example.

In a particular embodiment of the invention, the granules obtained at the end of step 6) are lubricated. Accordingly, following sizing, at least one lubricating substance selected from the lubricants conventionally employed in the pharmaceutical and nutraceutical fields is introduced into the oscillating granulator; more particularly, the lubricating substance is a mixture of talc and glycerol dibehenate.

It is then possible to package the above granules in the form of tablets, gelatin capsules or pastilles for sucking, for example. In that case, an additional step is necessary in which the granules are compressed to give tablets or pastilles for sucking.

In a particular embodiment of the invention, the ratio by weight (a)/(b) of the copolymers (a) and (b) in steps 1) and 4) of the process according to the present invention is identical.

It is also possible to carry out step 4) of the process of the present invention several times in succession and thus obtain a "multi-layer" system, that is to say a system composed of a granule of active ingredient according to steps 1) to 3) and then a succession of layers according to step 4). That system will be used according to the desired release profile of the active ingredient.

The Examples which follow are given by way of non-limiting examples.

EXAMPLE 1

Pharmaceutical Composition According to the Present Invention Based on Iron(II) Sulfate

| Raw materials | Unit formula: for 1 tablet |
|---|---|
| Iron(II) sulfate | qs for 80 mg of elemental iron |
| Maltodextrin | 25.00 mg |
| Microcrystalline cellulose | qs for a 350 mg tablet |
| Eudragit RS 30 D ® (aqueous suspension containing 30% dry material) | 45.67 mg |
| Eudragit RL 30 D ® (aqueous suspension containing 30% dry material) | 19.50 mg |

-continued

| Raw materials | Unit formula: for 1 tablet |
|---|---|
| Talc | 7.80 mg |
| Glycerol dibehenate | 8.00 mg |
| Triethyl citrate | 3.90 mg |
| Purified water | qs |
| Total unit weight | 350 mg expressed as dry material |

EXAMPLE 2

An Embodiment of the Process According to the Present Invention for the Preparation of Tablets having the Composition Given in Example 1

A) Dry mixing

There are introduced into a FIELDER® mixer:
iron(II) sulfate
maltodextrin
microcrystalline cellulose.

Mixing is carried out for 10 minutes at low speed to give a homogeneous mixture.

B) Preparation of the Coating Suspension

There are introduced into a container of sufficient capacity:
64% of the Eudragit® mixture in a ratio by weight Eudragit RS 30 D®/Eudragit RL 30 D® of approximately 65/35, previously filtered through a sieve of mesh size 0.4 mm
triethyl citrate (20% of the amount of Eudragit®, expressed as dry weight, per tablet).

Mixing is carried out for 10 minutes with stirring at moderate blade speed.

C) Coating

Coating of mixture A) is carried out with the aid of suspension B).

coating time of the inner phase=approximately 20 minutes.

Purified water is added to the coating, if necessary, until a mass capable of granulation is obtained.

D) Breaking Up

The moist mass is broken up on an oscillating granulator equipped with a screen having a mesh size of 3.15 mm.

E) Drying

The broken granule is dried in a fluidised-air bed to a residual humidity of the dried granule of from 2.5% to 3.5%.

F) Sizing

The granule dried in E) is sized on an oscillating granulator equipped with a screen of mesh size 1.5 mm.

G) Preparation of the Coating Suspension in a Fluidised-Air Bed

There are introduced into a container of sufficient capacity:
36% of the Eudragit® mixture in a ratio by weight Eudragit RS 30 D®/Eudragit RL 30 D® of approximately 65/35, previously filtered through a sieve of mesh size 0.4 mm.

The Eudragit® suspension is stirred and there are then introduced:
talc
triethyl citrate (20% of the amount of Eudragit®, expressed as dry weight, per tablet).

Stirring is continued until perfect homogeneity is achieved.

H) Coating of the Granules in a Fluidised-Air Bed

The dried and sized granules obtained in F) are introduced into the vessel of said fluidised-air bed.

The coating suspension prepared in G) (which is to be stirred constantly throughout the entire coating operation) is atomised onto the granules with the following parameters:
inlet air temperature: 40° C.
atomisation pressure: 2 bar
atomisation rate: 300 grams/minute
atomisation nozzle diameter: 1.2 mm.

The granules previously coated in the fluidised-air bed are dried to a residual humidity of the coated granules of from 2.5% to 3.5%.

Sizing

Sizing of the coated granules is carried out on an oscillating granulator equipped with a screen of mesh size 1.5 mm.

J) Lubrication

Following the sizing, there are introduced into the oscillating granulator equipped with a screen of mesh size 1.5 mm:
talc
glycerol dibehenate.

Mixing is carried out for 25 minutes.

The particle size distribution so obtained is as follows:
100% of the granules<1.5 mm
30% of the granules>0.71 mm
50% of the granules<0.355 mm,
the mean diameter being from 0.25 mm to 0.355 mm.

K) Compression

The lubricated granules are compressed on a rotary press equipped with D9 R9 dies.

Pharmacotechnical Parameters:
mean hardness (measurement carried out on Pharmatest® type PTB 301): 63 N (max. 71 N, min. 51 N)
friability: 100 turns (0.14%) (test of the friability of the tablets according to monograph 2.9.7 of the European Pharmacopoeia, current edition).

The invention claimed is:

1. A pharmaceutical or nutraceutical composition comprising at least one coated granule providing sustained release of an active ingredient which is an iron source, the coated granule being composed of a particle that comprises an iron source and is coated with at least two coatings, wherein the at least two coatings comprise a combination of excipients of:
   (i) at least one copolymer (a) of esters of acrylic acid and of methacrylic acid having a molar percentage of quaternary ammonium groups of less than or equal to 8%,
   (ii) a second copolymer (b) of esters of acrylic acid and of methacrylic acid having a molar percentage of quaternary ammonium groups of greater than 8%,
wherein a ratio by weight of (a)/(b) is 70:30, and wherein an amount of (a) is from 2.5% to 5.0% by dry weight based on the total weight of the composition, whereby the at least two coatings protect the iron source against oxidation and wherein the pharmaceutical or nutraceutical composition does not comprise an antioxidant.

2. The composition of claim 1, wherein the iron source is a source of iron(II) or iron(III) in the form of a salt or complex.

3. The composition of claim 2, wherein the iron salt is selected from sulfate, fumarate, gluconate, ascorbate, oxalate, succinate, glycerophosphate and feredetate.

4. The composition of claim 2, wherein the iron complex is selected from iron-dextran, iron-polymaltose and iron-protein complexes.

5. The composition of claim 1, wherein the iron source is iron(II) sulfate.

6. The composition of claim 1, wherein the molar percentage of quaternary ammonium groups in copolymer (a) is from 2% to 8%.

7. The composition of claim 6, wherein the molar percentage of quaternary ammonium groups in copolymer (a) is 5%.

8. The composition of claim 1, wherein copolymer (a) is Poly(ethyl acrylate-co-methyl methacrylate-co-trimethylammonioethyl methacrylate chloride) 1:2:0.1.

9. The composition of claim 1, wherein the molar percentage of quaternary ammonium groups in copolymer (b) is from about 8% to 12%.

10. The composition of claim 9, wherein the molar percentage of quaternary ammonium groups in copolymer (b) is 10%.

11. The composition of claim 1, wherein copolymer (b) is Poly(ethyl acrylate-co-methyl methacrylate-co-trimethylammonioethyl methacrylate chloride) 1:2:0.2.

12. The composition of claim 1, wherein the amount of copolymer (a) is from 3.5% to 4.0% by dry weight, based on the total weight of the composition.

13. The composition of claim 1, wherein the combination of excipients further comprises a diluent, a binder, a lubricant, an anti-agglomeration agent, a plasticizer, or a combination thereof.

14. The composition of claim 1, wherein the plasticizer is selected from acetyl tributyl citrate, acetyl triethyl citrate, acetylated fatty acid glycerides, castor oil, diethyl sebacate, dibutyl sebacate, glyceraol, glycerol monostearate, glyceryl triacetate, polyethylene glycol, polyoxyetheylenelpolyoxypropylene copolymers, propylene glycol, tributyl citrate, triethyl citrate, and combinations thereof.

15. The composition of claim 13, wherein the plasticizer is triethyl citrate.

16. The composition of claim 13, wherein the diluent is selected from celluloses and lactose.

17. The composition of claim 13, wherein the diluent is a cellulose.

18. The composition of claim 13, wherein the binder is selected from maltodextrins and povidones.

19. The composition of claim 13, wherein the binder is maltodextrin.

20. The composition of claim 1, wherein the pharmaceutical or nutraceutical composition is in oral form.

21. The composition of claim 20, wherein the oral form is selected from tablets, gelatin capsules, capsules, pastilles for sucking, and powders for drinkable suspensions and for syrups.

22. A method for the treatment and/or prevention of deficiencies of minerals and oligoelements comprising administering the composition of claim 1.

23. The method of claim 22 for the treatment and/or prevention of iron deficiencies with or without anemia.

24. The method of claim 22 for the treatment and/or prevention of iron deficiency in pregnant women.

25. A process for the preparation of a pharmaceutical or nutraceutical composition according to claim 1 comprising the following steps:
    (i) coating the active ingredient, in a blade mixer, with an aqueous dispersion of the two copolymers (a) and (b), wherein the ratio by weight of (a)/(b) is 70:30, and wherein an amount of (a) is from 2.5% to 5% by dry weight based on the total weight of the composition,
    (ii) breaking the granule obtained in i),
    (iii) drying the granules obtained in ii),
    (iv) coating the dried granules obtained in iii) in a fluidized-air bed by atomization of an aqueous dispersion of the two copolymers (a) and (b), wherein the ratio by weight of (a)/(b) is 70:30, and wherein an amount of (a) is from 2.5% to 5.0% by dry weight based on the total weight of the composition, and
    (v) drying the coated granules obtained in iv).

26. The process of claim 25 which does not involve these of an organic solvent.

27. The process of claim 25, wherein the granules obtained are packaged directly in the form of powder for a drinkable suspension or for syrup.

28. The process of claim 25 comprising an additional step wherein the granules are lubricated.

29. The process of claim 28, further comprising a step of compressing the granules to form tablets or pastilles for sucking, or forming gelatin capsules.

30. The process of claim 25, wherein step iv) is carried out several times in succession.

* * * * *